Figure 1:
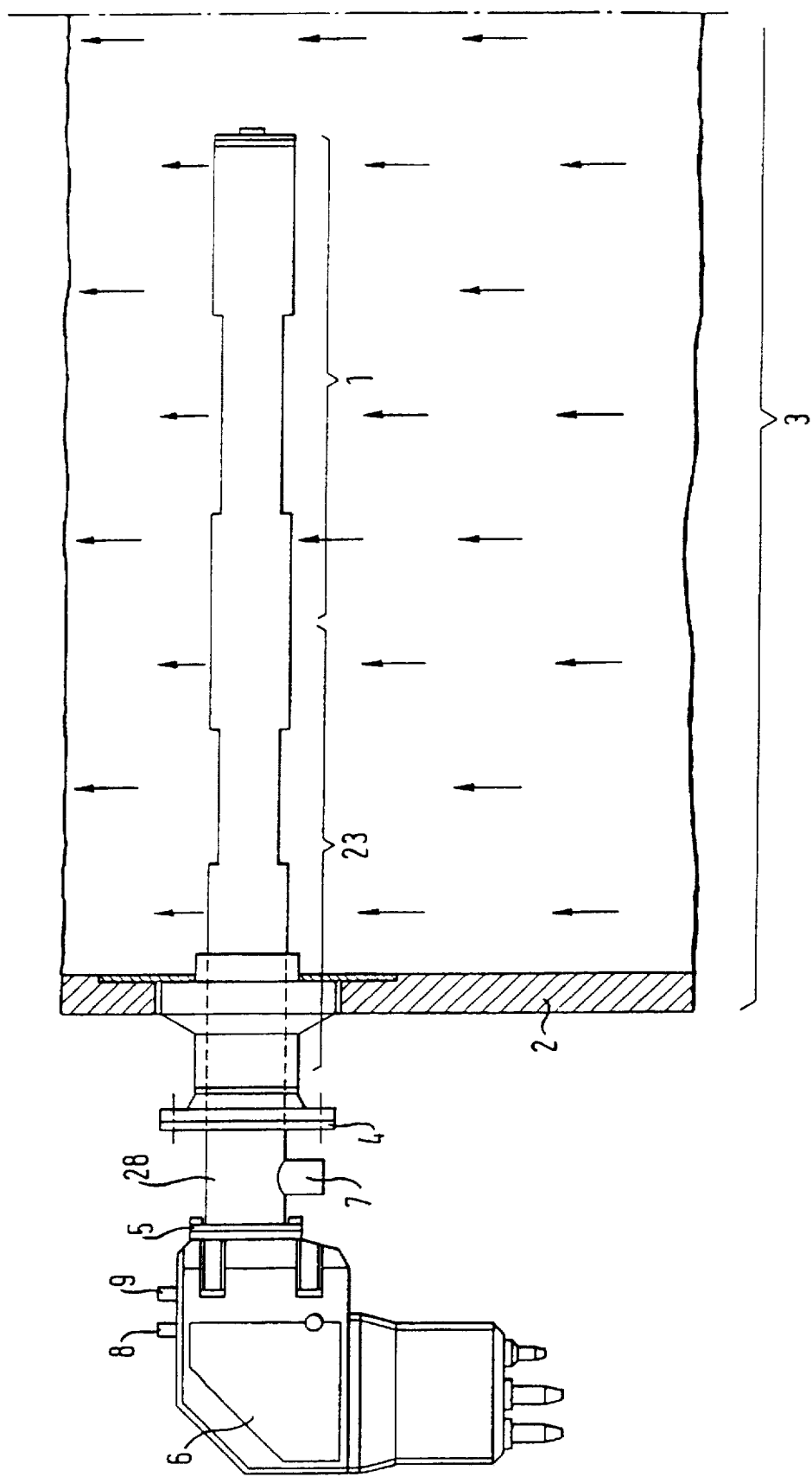

United States Patent [19]

Hartig et al.

[11] Patent Number: 5,781,306
[45] Date of Patent: Jul. 14, 1998

[54] MEASURING APPARATUS FOR GAS ANALYSIS

[75] Inventors: Wolfgang Hartig, Waldkirch; Jürgen Kaufmann, Denzlingen, both of Germany

[73] Assignee: Erwin Sick GmbH Optik-Elektronik, Waldkirch/Breisgau, Germany

[21] Appl. No.: 565,396

[22] Filed: Nov. 30, 1995

[30]  Foreign Application Priority Data

Dec. 2, 1994 [DE] Germany .................. 44 43 016.7

[51] Int. Cl.$^6$ .................................................. G01N 21/00
[52] U.S. Cl. .................. 356/436; 356/437; 250/373; 250/374
[58] Field of Search .................. 356/244, 246, 356/439, 438, 440, 73, 342, 436, 437; 250/339, 341, 343, 351, 373–375

[56]  References Cited

U.S. PATENT DOCUMENTS

| 3,861,809 | 1/1975 | Hall, Jr. ................... | 356/188 |
|---|---|---|---|
| 4,126,396 | 11/1978 | Hartmann et al. ............ | 356/434 |
| 4,560,873 | 12/1985 | McGowan et al. ............ | 250/339 |
| 5,241,368 | 8/1993 | Ponstingl et al. ............ | 356/436 |

FOREIGN PATENT DOCUMENTS

| 35 03 720 A1 | 8/1986 | Germany . |
|---|---|---|
| 41 33 701 A1 | 4/1993 | Germany . |
| 41 35 843 A1 | 5/1993 | Germany . |

*Primary Examiner*—Frank G. Font
*Assistant Examiner*—Michael P. Stafira
*Attorney, Agent, or Firm*—Townsend and Townsend and Crew LLP

[57]  ABSTRACT

A spectrometric gas measurement apparatus for the determination of the presence and/or concentration of gases in a spatial region has a spectrometric measurement head which transmits into the spatial region measurement radiation having the spectral ranges necessary for the determination of the gases. Furthermore, a reflector is provided at the spatial region which reflects the light which is passed through at least a part of the spatial region back to the measurement head where it is split up spectrally in an analyzer and then supplied to a photoreceiver arrangement. A measurement tube extending in the direction of light propagation is provided in the spatial region through which the measurement light passes. The measurement tube has a transverse throughflow opening, is closed at the end remote from the measurement head, accommodates the retro-reflector, and is also supplied at both ends of the transverse throughflow opening with flushing air which stands at a slight excess pressure relative to the spatial region. A reference tube with an audit cell is inserted in front of the measurement tube.

27 Claims, 3 Drawing Sheets

MEASURING APPARATUS FOR GAS ANALYSIS

The invention relates to a measuring apparatus for gas analysis in accordance with the preamble of patent claim 1.

Such gas measuring apparatuses are, for example, provided at exhaust ducts, in order to determine the noxious gases contained in the exhaust gas flow, in particular $SO_2$, NO, $NH_3$, CO and the like, with respect to their concentration.

DESCRIPTION OF THE KNOWN PRIOR ART

There are essentially two principles which are known today for the realisation of this measurement task:

1. The in situ principle

In in situ measurement the concentration of the gas burden is directly determined by spectrometric measurement in the main exhaust gas flow.

2. The extraction principle

With extraction measurement, a part-quantity of gas is drawn out of the main gas flow, is prepared and is supplied to an outside measurement location/measurement device. The total concentration of the main gas flow is then calculated from the determination of the concentration of the partial gas flow. After the measurement, the partial gas flow is led back again to the exhaust gas flow.

Both measurement principles have advantages and disadvantages and the different embodiments belong nowadays to the prior art.

The invention present here belongs to the group of the in situ systems and describes a special measurement tube which projects into the exhaust gas duct, through which exhaust gas flows, and which thereby enables, together with a measurement head mounted at the outer wall of the exhaust gas duct, the continuous measurement of the gas flow without changing the latter. During this measurement, a measurement path is irradiated, starting from an electromagnetic radiation source, the spectrum of which transmits at least the spectral ranges required for the measurement of the gases to be determined. At the end of the measurement path the radiation is essentially reflected back on itself by a reflector provided for this purpose, is spectrally broken down in an analyser and is then led to a photoreceiver arrangement. During this, electrical signals are generated which are respectively associated with a particular wavelength, or with a narrow wavelength range, which are supplied to an electronic evaluation circuit and thereby enable the determination of the gas concentration in dependence on the signals that are received.

DISADVANTAGES OF THE KNOWN PRIOR ART

It is however problematic with these spectrometric gas measuring devices that the measuring tube which projects into the exhaust gas duct is directly exposed to an environmental burden which is in part extreme (contamination, temperature, aggressive media) and therefore the ability of the measurement tube to function can only be achieved over reasonable periods of time with considerable cost and complexity.

It is known in this connection to surround the gas measuring region within the measurement tube with a porous, gas-permeable ceramic sleeve which separates out dust particles and to blow this free, i.e. clean it, by cyclical phases of excess pressure.

On the other hand, it is necessary to check the long-term stability of the measured value at regular intervals (frequently a requirement of the regulating authority for these measurement systems) in order to be able to achieve the required measurement reliability.

The carrying out of these reference cycles through the insertion of a cell (cuvette) filled with a reference or calibration gas into the beam path likewise belongs to the prior art.

A disadvantage of this prior art is to be seen in the fact that this reference cell is arranged outside of the exhaust gas flow and thus has a different temperature behaviour from the actual exhaust gas flow when the reference cell and the exhaust gas flow, i.e. the reference gas temperature and the exhaust gas temperature are not at the same value, this leads to measurement errors and must be corrected or compensated for by complicated correction measures.

OBJECT OF THE INVENTION

The object of the invention is now to provide an apparatus for spectrometric gas measurement which delivers stable measurement results with a cost and complexity which is as low as possible and at the same time, however, with a high reliability and working life.

SOLUTION OF THE OBJECT

To satisfy this object there are provided the features of the characterising part of patent claim 1. Further advantageous developments of the invention are characterised by the subordinate claims.

In accordance with the invention, an open gap opening through which the measurement gas can freely flow is thus provided within the measurement tube. The optically effective bounding of the gap opening is ensured on both sides in the measurement tube axis by an excess air pressure in the interior of the measurement tube. This air cushion at the edge of the gap opening is built up by external spectrally neutral flushing air which emerges via two ring flanges into the interior of the measurement tube. Through this measure it is achieved that outside of the measurement gap the lance has exhaust gas free and clean spaces in the interior in which further optical components necessary for the function can be arranged, such as for example the retro-reflector. The pressure in the flushing gas spaces may, however, only be higher than in the surrounding spatial region by an amount such that no exhaust gas located in the spatial region penetrates into the flushing gas channels but, on the other hand, such that the flushing gas does not displace a notable quantity of exhaust gas away from the transverse throughflow opening.

Furthermore, to satisfy the required long-term stability of the measurement results, a reference tube with an audit cell sealed relative to the exhaust gas flow can be inserted into the measurement tube between the spectrometric measurement head and the measurement tube. In order for this audit cell to stand in thermal equilibrium with the exhaust gas flow in a manner which is as ideal as possible further openings are provided in the reference tube so that the cell can be directly flushed by the exhaust gas flow and is thus thermally balanced. Through this serial arrangement of the audit cell and measurement gap (considered in the optical beam direction) it is possible to ensure a simple operation, both in the measurement phase and also in the reference phase, which is reliable in its principle.

ADVANTAGES OF THE INVENTION

The advantages which result from the execution of the measurement tube in accordance with the invention are to be seen in the fact that the gas flow, which is to be measured, is passed almost unhindered and uninfluenced through the measurement gap and thus available for the measurement in unadulterated manner. Likewise, an adaptation of sensitivity can be carried out relative to the installation-dependent state of the exhaust gas flow, at least within limits, via the effective measurement gap length. Moreover, the audit cell, which is located in the reference tube and which can be externally filled with various reference gases of different concentrations, makes it possible for the spectrometric measurement head to determine the reference values on the same optical path as for the actual exhaust gas measurement.

DESCRIPTION OF EXAMPLES OF THE INVENTION

The invention will be described in the following by way of example and with reference to the drawing in which are shown:

FIG. 1 a partly sectioned side view of a gas measuring apparatus in accordance with the invention mounted at an exhaust gas duct, FIG. 2 a view of the subject of FIG. 1 from below without the measurement head and without the wall of the exhaust gas duct, and FIG. 3 a section of the subject of FIG. 2 on the line III—III.

In FIG. 1 there is shown schematically a section through a spectrometric gas measurement apparatus in accordance with the invention. In FIG. 1 it can be seen that a combined measurement and reference tube 1, 23, which extends in an exhaust gas duct 3 transversely to the flow direction shown by arrows, is secured to the outer wall 2 of the exhaust gas duct by a releasable wall connection 4. A spectrometric measurement head 6 is screwed on to the end of the tube outside the exhaust gas duct 3 via a connection flange 5. Furthermore, FIG. 1 schematically shows a flushing air supply tube 28, with a lateral inflow stub 7 for externally supplied flushing air between the connection flange 5 and the wall connection 4. In addition to the electrical supply and signal output lines from and to the spectrometric measurement head 6, which are not further illustrated here, a test gas inlet opening 8 and also a test gas outlet opening 9 are indicated.

Figure 2:
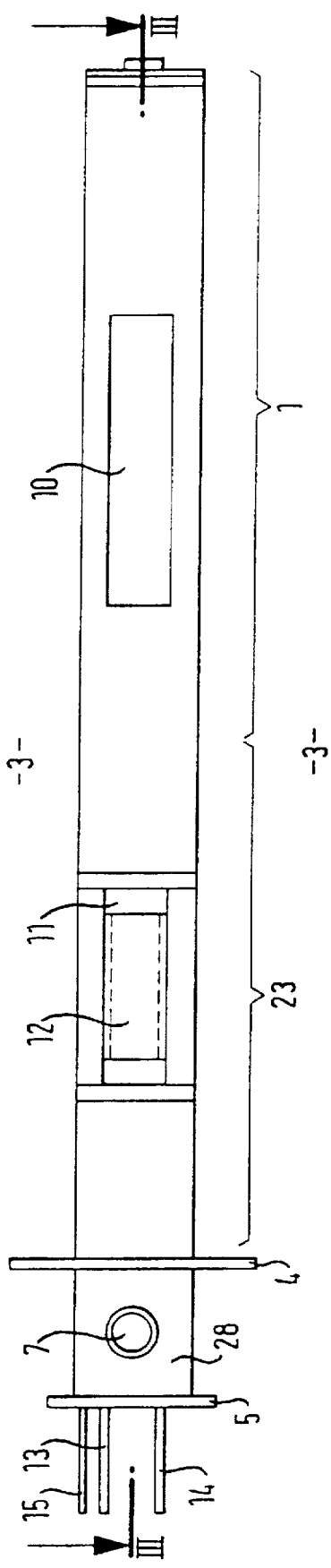

It is evident from FIG. 2 that a rectangular transverse throughflow opening in the form of a measurement gap 10 is present in the measurement tube 1, with the measurement gas flowing through the transverse throughflow opening over a defined cross-section. In the reference tube 23, which is inserted before the measurement tube 1, there is provided a further transverse throughflow opening in the form of a reference gap 11 which extends parallel to the measurement gap 10. Within the reference gap 11 there is located an audit cell 12 which is described in detail further below and is in direct contact with the exhaust duct 3 surrounding the measurement tube 1 and the reference tube 23.

The supply line 13 and the discharge line 14 for the reference gas for the audit cell 12 are visible through the connection flange 5 which closes off in ring-like manner one side of the flushing air supply tube 28 which adjoins the inlet to the reference tube 23. A mechanical slide rod 15 serves to control the zero-point reflector 18 which will be described in detail in the following with reference to FIG. 3.

Figure 3:
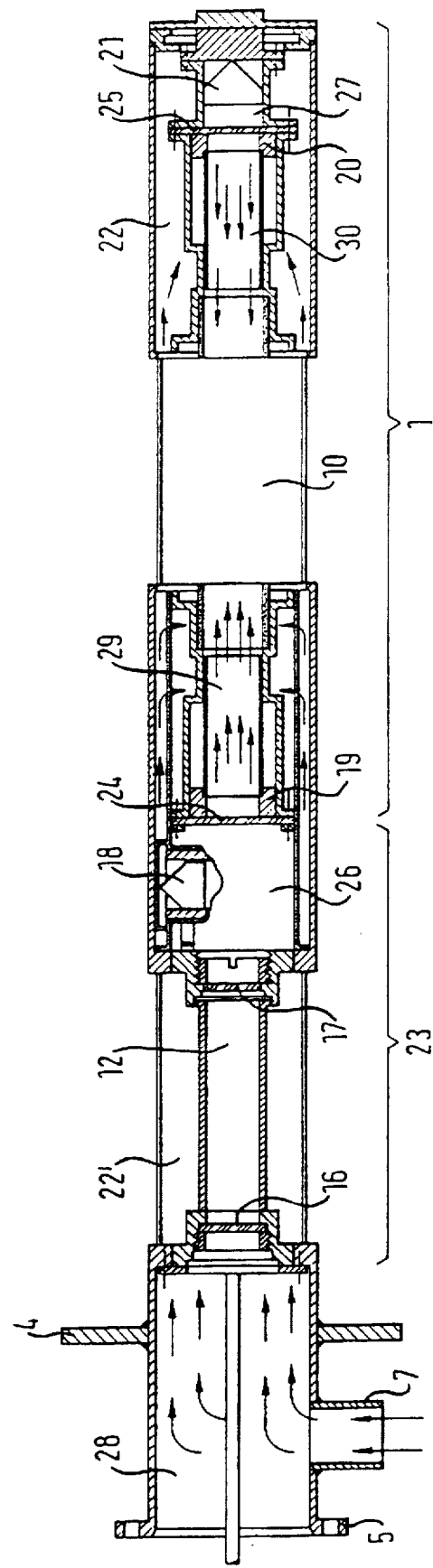

The relative arrangement of the individual components of the gas measuring apparatus of the invention can be seen from the following description of the operation with respect to FIG. 3.

The electromagnetic radiation enters into the inner space of the reference tube 23 at the connection flange side and passes via the cell window 16 into the audit cell 12. The radiation emerges through the cell window 17. If the measurement system is located in the measurement gas phase, the audit cell 12 is filled with a spectrally neutral atmosphere, i.e. no reference gas is located in the interior. In like manner, the zero-point reflector 18, as shown in FIG. 3, is also parked in the outwardly pivoted position. The electromagnetic radiation can thus enter unhindered into the measurement tube 1 and then pass through the ring flange 19, the measurement gap 10, and a further ring flange 20 to a retro-reflector 21. At this retro-reflector 21 the emerging radiation is reflected back on itself in auto-collimation. The radiation now passes through the measurement tube 1 again in the reverse sequence, so that the radiation enters again into the measurement head 6 after having been spectrally influenced in dependence on the optical filter action of the gas being measured.

With the aid of an analyser present in the measurement head, this radiation is split up spectrally and thereafter supplied to a photoreceiver arrangement. With this electrical signals are generated which are respectively associated with a specific wavelength or with a narrow wavelength range. The signals are then processed in an electronic evaluation circuit and thus enable the determination of the gas concentration in the measurement gas region. It is then possible to calculate the total concentration in the exhaust gas duct 3 by way of a conversion factor, which can be found through calibration,.

In order to achieve the required long-term stability of the measurement system, the audit cell 12 is cyclically filled (typically 1 to 3 times a day) via the feedline 13 with gases of precisely known but differing concentrations (low, medium, high). For this purpose the zero-point reflector 18, which is parked in the measurement system, is pivoted into place under program control via a slide rod 15, which is for example electrically driven. The radiation is thus already reflected back at the output of the audit cell 12 and is spectrally split up and evaluated in equivalent manner to the previously described method. Since, however, the concentration of the gas in the audit cell 12 is known in these cases, the measured value found can be used as a reference. Through the different concentration states of the reference gas, it is furthermore possible to determine the total dynamic behaviour of the measurement system at several support locations and to take account of it in the evaluation circuit.

In order to keep the inner space of the measurement tube 1 clean over longer periods of time, even with severe operating conditions, clean flushing air is blown via the two ring flanges 19 and 20, from flushing air tube regions 29, 30, into end regions remote from the measurement gap 10, in the direction of the measurement gap 10, in order to thus close off the flushing air tube regions 29, 30 with an air buffer. In this manner, a low excess air pressure arises in the interior of the measurement tube 1 relative to the measurement gap 10 which prevents the penetration of contamination via the measurement gap.

Alternatively, a cover disk 24, 25, which is transparent for the spectral range which is used, can be additionally built in in front of the ring flange 19, or in front of the ring flange 20, in order, in the case of a breakdown (for example failure of the flushing air system) to avoid contamination of the spaces 26, 27 in the region of the zero-point reflector 18 and of the retro-reflector 21 respectively.

In accordance with the invention, the outer wall of the measurement tube 1 and of the reference tube 23 are partly executed as a twin-walled closed circular segment, so that air channels 22, 22' are thereby formed for the supply of flushing air to the ring flanges 19 and 20. This constructional design is additionally to be regarded as positive because the mechanical stability of the measurement tube is thereby substantially increased.

More specifically the flushing air or other flushing medium passes through apertures (not shown) provided in the flanges at the right hand end of the air supply tube 28 in FIG. 3 into at least one of the channels 22' formed on either side of the audit cell 12 and from there via apertures (not shown) in the flange at the right hand end of the audit cell 12 into the outer ring space surrounding the air tube region 29. Part of the flushing medium then flows through apertures in the intermediate walls surrounding the air supply tube 29 and in the ring flange 19, and/or through apertures formed in the left hand end of the air supply tube 29, into the left hand end of the air supply tube 29 from which it escapes into the measurement gap 10 via the right hand end of the air supply tube. The remainder of the flushing medium not entering the air supply tube 29 passes on either side of the measurement gap 10 through ducts formed between the outer tube wall and inner tube wall sections on either side of the measurement gap 10 into the channel 22. From here it passes through apertures (not shown) into the space 27 and/or through the disc 25 and/or through the ring flange 20, and/or through apertures in the wall of the air supply tube 30, into the latter. The flushing medium then escapes from the left hand end of the air supply tube in FIG. 3 into the measurement gap 10.

Alternative arrangements are also possible. For example, the flushing medium could be led via armoured hoses or pipes from the plenum chamber formed in the tube section 28 to the left hand end of the air supply tube 29 and to the right hand end of the air supply tube 30.

What is claimed is:

1. A spectrometric gas measuring apparatus for determining the presence of gases in a spatial region, the apparatus comprising:
    a spectrometric measurement head that is mountable at the spatial region including an irradiation source and an analyzer, the irradiation source transmitting measurement beams having spectral ranges required for the determination of the gases into the spatial region;
    a measurement reflector at the spatial region that reflects light that has passed through at least a portion of the spatial region back to the measurement head, the light being spectrally broken down in the analyzer;
    a photoreceiver arrangement that receives the spectrally broken down light from the analyzer and generates electrical signals that are respectively associated with a specific wavelength, the electrical signals being applied to an electronic evaluation circuit that determines the presence of the gases; and
    a measurement tube in the spatial region through which the measurement radiation passes, the measurement tube extending in a direction of light propagation and having a transverse throughflow opening communicating with the surrounding spatial region, the measurement tube being closed at an end remote from the measurement head and accommodating the measurement reflector, the measurement tube being supplied at both ends of the transverse throughflow opening with a spectrally neutral flushing gas relative to a spectral measurement range at a slightly higher pressure relative to the spatial region.

2. A gas measuring apparatus in accordance with claim 1 wherein the transverse throughflow opening extends in the direction of flow of the gas located in the spatial region.

3. A gas measuring apparatus in accordance with claim 1 wherein the flushing gas supply is provided into end regions of the measurement tube remote from the transverse throughflow opening.

4. A gas measuring apparatus in accordance with claim 1 wherein the transverse throughflow opening is formed as a transverse gap.

5. A gas measuring apparatus in accordance with claim 1 wherein the measurement tube is double-walled and the inner space of the double wall serves for the supply of flushing gas.

6. A gas measuring apparatus in accordance with claim 1 wherein a reference tube is inserted in front of the tube which is likewise traversed by the measurement radiation; wherein a reference cell, which can be filled in a defined manner with one or more reference gases, is provided in the reference tube and is closed off at least relative to the measurement tube; and wherein a zero-point reflector, which can be swung in and swung out, is provided at the end of the reference tube adjacent the measurement tube.

7. A gas measuring apparatus in accordance with claim 6 wherein the zero-point reflector is arranged in a space which is closed off at both ends by a window.

8. A gas measuring apparatus in accordance with claim 1 wherein space in front of the measurement reflector is closed off by a window.

9. A gas measuring apparatus in accordance with claim 6 wherein a further transverse throughflow opening is provided in the region of the reference cell.

10. A gas measuring apparatus in accordance with claim 9 wherein the further transverse throughflow opening extends in a direction of flow of gas located in the spatial region.

11. A gas measuring apparatus in accordance with claim 6 wherein the reference tube is of double-wall design, wherein an inner space of the double wall serves as a supply for flushing gas, and wherein measurement tube inner spaces and reference tube inner spaces are in flow communication.

12. A gas measuring apparatus in accordance with claim 6 wherein the reference cell is an audit cell.

13. A gas measuring apparatus in accordance with claim 6 wherein a flushing gas supply tube is inserted in front of the measurement tube.

14. A gas measuring apparatus in accordance with claim 6 wherein a flushing gas supply and extraction line is provided at an entrance to the reference tube.

15. A gas measuring apparatus in accordance with claim 6 wherein a thrust rod extends to the zero-point reflector in the reference tube.

16. A gas measuring apparatus in accordance with claim 6 wherein the measurement tube and the reference tube are formed as a one-piece tube structure.

17. A gas measuring apparatus in accordance with claim 1 wherein the measurement reflector comprises a retroreflector.

18. A gas measuring apparatus in accordance with claim 1 wherein the photoreceiver arrangement generates electrical signals that are respectively associated with a specific range of wavelengths as opposed to a specific wavelength.

19. A gas measuring apparatus in accordance with claim 1 wherein the electronic evaluation circuit determines the concentration of gases.

20. A gas measuring apparatus in accordance with claim 1 wherein the neutral flushing gas comprises flushing air.

21. A gas measuring apparatus in accordance with claim 6 wherein the reference tube is closed off relative to the measurement head by a window.

22. A gas measuring apparatus in accordance with claim 13 wherein the flushing gas supply tube is inserted in front of the reference tube.

23. A gas measuring apparatus in accordance with claim 14 wherein the flushing gas supply and extraction line extends through the measurement head.

24. A gas measuring apparatus in accordance with claim 14 wherein the flushing gas supply and extraction line extends through the flushing gas supply tube.

25. A gas measuring apparatus in accordance with claim 15 wherein the thrust rod extends through the entrance to the reference tube.

26. A gas measuring apparatus in accordance with claim 25 wherein the thrust rod extends through the flushing gas supply tube.

27. A gas measuring apparatus in accordance with claim 25 wherein the thrust rod extends through the measurement head.

* * * * *